(12) United States Patent
Cojocariu et al.

(10) Patent No.: US 9,745,533 B2
(45) Date of Patent: Aug. 29, 2017

(54) AQUEOUS LUBRICANT COMPOSITION (71) Applicant: Church & Dwight Co., Inc., Princeton, NJ (US)

(72) Inventors: Cristina Cojocariu, Bridgewater, NJ (US); Michael J. Harrison, Princeton, NJ (US); D. Craig Woodward, Plano, TX (US); Justin Lee Batson, Mansfield, TX (US); Dennis R. Blum, East Brunswick, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 3 days.

(21) Appl. No.: 14/773,036

(22) PCT Filed: Mar. 14, 2014

(86) PCT No.: PCT/US2014/027014
§ 371 (c)(1),
(2) Date: Sep. 4, 2015

(87) PCT Pub. No.: WO2014/152154
PCT Pub. Date: Sep. 25, 2014

(65) Prior Publication Data
US 2016/0017254 A1    Jan. 21, 2016

Related U.S. Application Data (60) Provisional application No. 61/781,599, filed on Mar. 14, 2013.

(51) Int. Cl.
C10M 161/00    (2006.01)
C10M 173/02    (2006.01)
(Continued)

(52) U.S. Cl.
CPC ............ *C10M 161/00* (2013.01); *A61F 6/04* (2013.01); *A61K 9/0034* (2013.01); *A61K 9/06* (2013.01);
(Continued)

(58) Field of Classification Search
CPC ...... C10M 161/00; A61F 6/04; A61K 9/0034; A61K 9/06; A61K 47/36
USPC ................................. 508/309, 506, 219, 175
See application file for complete search history.

(56) References Cited

U.S. PATENT DOCUMENTS

| | | | |
|---|---|---|---|
| 4,869,270 A | | 9/1989 | Ueno et al. |
| 5,595,980 A | * | 1/1997 | Brode .................. A61K 9/0014 424/DIG. 14 |

(Continued)

FOREIGN PATENT DOCUMENTS

| | | |
|---|---|---|
| EP | 2559708 A1 | 2/2013 |
| EP | 2249799 B1 | 3/2013 |

(Continued)

OTHER PUBLICATIONS

Begay, et al., "Identification of Personal Lubricants That Can Cause Rectal Epithelial Cell Damage and Enhance HIV Type 1 Replication in Vitro", AIDS Research and Human Retroviruses, vol. 27, pp. 1-6, 2011.

(Continued)

*Primary Examiner* — James Goloboy
(74) *Attorney, Agent, or Firm* — Church & Dwight Co., Inc.

(57) ABSTRACT

The present invention is directed towards an aqueous lubricant composition comprising hyaluronic acid, organic acid, salts and water, and has a pH of between 5.5 and 7.0 and an osmolality between about 150 and 1,500 mOsm/kg. The (Continued)

lubricant surprisingly has long-lasting lubricity and low osmolality as compared to conventional lubricants on the market.

16 Claims, 8 Drawing Sheets

(51) Int. Cl.
| | |
|---|---|
| *C10M 119/20* | (2006.01) |
| *C10M 125/18* | (2006.01) |
| *A61K 9/00* | (2006.01) |
| *A61K 9/06* | (2006.01) |
| *A61K 47/36* | (2006.01) |
| *A61F 6/04* | (2006.01) |

(52) U.S. Cl.
CPC .......... *A61K 47/36* (2013.01); *C10M 173/02* (2013.01); *C10M 2207/022* (2013.01); *C10M 2207/122* (2013.01); *C10M 2207/123* (2013.01); *C10M 2209/126* (2013.01)

(56) References Cited

U.S. PATENT DOCUMENTS

| | | | |
|---|---|---|---|
| 5,885,591 A | 3/1999 | Ahmad et al. | |
| 6,139,848 A | 10/2000 | Ahmad et al. | |
| 6,780,443 B1 | 8/2004 | Nakatsu et al. | |
| 7,030,273 B1 | 4/2006 | Sun | |
| 7,758,887 B2 | 7/2010 | Ahmad et al. | |
| 8,053,398 B2 | 11/2011 | Harrison | |
| 2004/0192642 A1* | 9/2004 | Yang | A61F 13/2051 514/54 |
| 2006/0159645 A1 | 7/2006 | Miller et al. | |
| 2006/0204557 A1 | 9/2006 | Gupta et al. | |
| 2008/0103214 A1* | 5/2008 | Schaub | A61K 9/0034 514/781 |
| 2009/0088405 A1 | 4/2009 | Kehoe et al. | |
| 2009/0143331 A1 | 6/2009 | Stroumpoulis et al. | |
| 2010/0284937 A1* | 11/2010 | Zhao | A61K 9/0034 424/43 |
| 2011/0171286 A1 | 7/2011 | Gousse et al. | |

FOREIGN PATENT DOCUMENTS

| | | | | |
|---|---|---|---|---|
| GB | WO 2009095639 A2 * | 8/2009 | | A61K 8/73 |
| WO | 2007/062995 A2 | 6/2007 | | |

OTHER PUBLICATIONS

Wolf, "Studies Raise Questions About Safety of Personal Lubricants", Chemical & Engineering News, vol. 90, Issue 50, pp. 46-47, Dec. 10, 2012.

* cited by examiner

AQUEOUS LUBRICANT COMPOSITION

REFERENCE TO RELATED APPLICATIONS

This application is related to U.S. Provisional Application Ser. No. 61/781,599 filed Mar. 14, 2013, as well as PCT Application No. PCT/US2014/027014 filed Mar. 14, 2014, and takes priority therefrom.

FIELD OF THE INVENTION

This invention is directed towards an aqueous lubricant composition and its method of production thereof.

BACKGROUND OF THE INVENTION

Lubrication is the process or technique that reduces wear of one or both surfaces that move relative to each other in close proximity. Lubricants prevent or lessen wear and irritation between the surfaces.

Personal lubricants for intercourse are well known and are useful for providing lubricity to various parts of the body, such as mucous membranes (e.g. oral, rectal, vaginal). These compositions may be in the form of jellies, liquids, vaginal suppositories, oils or emulsions. When applied onto condoms, these lubricants also facilitate unrolling of the condom as well as preventing the surfaces of the rolled condom from sticking together as the products age in storage.

Water-based personal lubricants are water-soluble and are the most widely used personal lubricants. These lubricants are easy to clean up, non-staining to fabrics and are formulated to be nonirritating. The viscosity of these products can be altered by adjusting their water content and concentration of cellulose or other gel-forming hydrophilic ingredients. However, because water-based personal lubricants absorb into the skin and mucous membranes and evaporate, these lubricants have a tendency to dry out during use. Very often, the water-based lubricant has to be reapplied to extend the intimate activity. This is one of the chief drawbacks of water-based lubricants, since reapplication is distracting and "breaks the mood".

To improve product lubricity, water-based lubricants are often formulated with high levels of polyhydric alcohols such as propylene glycol, glycerin or sorbitol that function as humectants. For example, the marketed K-Y® NATURAL FEELING® Liquid, which is described in U.S. Pat. No. 5,885,591 to Ahmad, et al. comprises about 30% glycerin, about 5% propylene glycol and about 10% sorbitol. In addition to polyhydric alcohols, surfactants are also added to water-based lubricants to reduce the attraction between water molecules, thereby making the lubricants more slippery and less sticky. For example, commercially available water-based lubricants of the ASTROGLIDE® series all contain surfactants such as polyquaternium-15.

Recent studies have shown that personal lubricants that contain polyhydric alcohols or surfactants may damage the vagina and rectum cell linings, potentially making the user more vulnerable to sexually transmitted diseases (STDs) (see O. Begay et al., *AIDS Research and Human retroviruses*, 27, 1-6, 2011; L. K. Wolf *C&EN* 90(50), 46-49, 2012). According to O. Begay, et al., the damaging effect is dependent upon osmolality of the lubricant. Osmolality is a parameter that indicates the overall concentration of the molecular ingredients in a composition. Osmolality is measured in moles (osmoles) of solute per kilogram of solvent. Mice that were exposed to lubricants with high osmolality were more susceptible to infections. Many water-based lubricants on the market have high osmolality, as they contain large amounts of ingredients such as propylene glycol, glycerin and sorbitol, which contribute to high numbers of moles of solutes per kg of solute.

A preferred type of personal lubricant is silicone-based. Silicone-based personal lubricants are very lubricious and do not dry out. Further, they are hypoallergenic, safe to use with condoms and are less damaging to cells because of their low osmolality. However, the main drawback of silicone-based lubricants is that they are greasy and can be difficult to cleanup.

To deliver the benefits of both water- and silicone-based lubricants, oil-in-water (o/w) emulsions-based lubricants have been developed and marketed. These lubricants are typically opaque or "milky" in appearance, which is caused by the difference in refractive index between the aqueous phase and the oil phase. LIQUID SILK® and SYSTEM JO® Hybrid are examples of emulsion-based personal lubricants.

To make the emulsion lubricants clear and transparent, and thus more appealing to consumers, two approaches have been taken. The first approach involves matching the refractive index between the two immiscible phases. The second approach involves the use of high concentrations of emulsifiers to form micro-emulsions. The oil droplets in the micro-emulsions are smaller than the light wavelength, thus making the emulsion appear clear. U.S. Pat. No. 6,139,848 to Ahmad, et al. discloses micro-emulsion-based lubricants, which are highly lubricious, clear and transparent. However, these micro-emulsion-based lubricants also have high levels of polyhydric alcohols (up to 45% w/w), which may harm vaginal cells.

An alternative to known water-based and silicone-based personal lubricants has been developed using hyaluronic acid ("HA") as a lubricating component to relieve vaginal dryness. For example, U.S. Patent Application No. 2010/0284937 to Zhao, et al. teaches a vaginal lubricant comprising a high molecular weight HA and a low molecular weight component selected from low molecular weight HA and chitosan, wherein the low molecular weight component stabilizes the lubricant.

U.S. Patent Application No. 2009/0143331 to Strompoulis, et al., teaches a cosmetic composition comprising at least one polysaccharide such as HA and encapsulating at least one inhibitor of degradation into the polysaccharide.

U.S. Pat. No. 4,869,270 to Uneo, et al., teaches a condom comprising a coating made from polysaccharide such as HA, wherein the coating is an aqueous solution that contains 10-70% concentration of the HA.

U.S. Patent Application No. 2011/0171286 to Cecile, et al., teaches an HA gel formulation for treating skin, comprising hyaluronic acid and at least one additional constituent selected from the group consisting of vitamin B, C and E, wherein the formulation exhibits greater stability.

However, the exemplary prior art either teaches a composition that requires a special ingredient to stabilize the HA, a high amount of HA of at least 10%, or the viscosity of the taught composition is undesirably low, causing the lubricant to be too watery and being retained poorly during contact in sexual intercourse.

Therefore, there continues to be a need for new personal lubricants that impart some of the benefits of both water-based lubricants (clear, easy to clean, non-staining) and silicone oil-based lubricants (highly lubricious, low osmolality). More specifically, there is a need for novel lubricants that match closely to the vaginal fluid to provide a natural alternative to commercially available personal lubricants.

Furthermore, the lubricants should be compatible with lubricated and non-lubricated latex, polyurethane and synthetic PI condoms.

SUMMARY OF THE INVENTION

The present invention is directed towards an aqueous lubricant composition comprising hyaluronic acid ("HA") as a moisturizing component and an aqueous carrier.

BRIEF DESCRIPTION OF THE DRAWINGS

For a better understanding of the nature and advantages of the present invention, one should refer to the details below in conjunction with the accompanying drawings.

DETAILED DESCRIPTION OF THE INVENTION

The present invention provides an aqueous lubricant composition comprising at least one moisturizing component in the form of HA and water, wherein the composition contains minimal amounts of polyhydric alcohols. The composition also provides surprisingly long lasting lubricity and low osmolality when compared to aqueous-based, silicone-based or emulsions-based lubricants. The composition of this invention can be used as a personal lubricant or can be applied to condoms prior to packaging.

In general, the composition comprises at least one HA moisturizing agent, a rheology modifier, at least one organic acid, at least one salt, optionally urea, and preferably at least one preservative and water. The composition may include additional components to enhance dermatological acceptability. "Dermatological acceptability" means that the composition resembles the vaginal fluid as much as possible, and does not cause irritation, infection or discomfort to the user's mucous membrane or skin. The vaginal fluid is mostly composed of water, electrolytes (e.g., sodium, potassium, chloride, magnesium, calcium), proteins (e.g., albumin), carbohydrates (e.g., glycogel, glucose), organic acids (e.g., lactic acid, acetic acid) and other organics (e.g., glycerol) (see G. R. Huggins et al., *Clin. Obstet. Gynecol* 24, 1175-80, 1981). D. F. Katz developed a vaginal fluid simulant having the same physical and chemical properties known to influence intravaginal gel efficacy (see D. F. Katz, et. *Contraception*, 59, 91-95, 1999).

The moisturizing agent of the present invention is the water-absorbing polymer hyaluronic acid ("HA"). The pharmaceutically acceptable salts of hyaluronic acid include both the salts with inorganic bases (e.g. sodium salt, potassium salt, ammonium salt, etc.) and the salts with organic bases (e.g. diethanolamine salt, cyclohexylamine salt, amino acid salt, etc.). Preferred salts are dermatologically acceptable ones. Typically, the HA of the present aqueous lubricant composition is obtained from animal sources or from bioprocesses, including via bacterial or enzyme synthesis. Suitably, the HA of the lubricant of the present invention is obtained from fermentation or enzymatic synthesis.

The present aqueous lubricant composition preferably comprises HA produced from the microorganism *Bacillus subtilis*, or by fermentation of *Streptococcus* species. Suitably all of the HA of the present aqueous lubricant composition is produced by fermentation of a *Streptococcus* sp.

The purity of HA is partially or wholly dependent on its source and its method of production. Typically, the purity of the HA used is at least 70%, preferably at least 85% and more preferably at least 90%. In particular, the HA used in the lubricant of the present invention suitably includes a heavy metal impurity level of less than 10 ppm, advantageously less than 5 ppm.

Further, the HA may be modified or unmodified. Useful HA may be modified by crosslinking to obtain at least one low level functional group or at least one peptide. The HA for the present aqueous lubricant is preferably unmodified. The preferred hyaluronic acid has a molecular weight of 40 kDa to 3 MDa, preferably 800 kDa to 2.0 MDa, more preferably 1.3 MDa to 1.8 MKDa. The moisturizing agent is present in an amount of from about 0.05 wt. % to about 5.00 wt. %, preferably from about 0.1 wt. % to about 2.0 wt. %, more preferably from about 0.4 wt. % to about 1.0 wt. % of the aqueous lubricant composition.

The rheology modifier of the present invention is selected from dimeric and trimeric fatty acids, amides, synthetic polymers and mixtures thereof. Preferably, the rheology modifier is a water-soluble polymer such as modified cellulose, selected from hydroxyethyl cellulose, carboxymethyl cellulose, hydroxypropyl cellulose, methylcellulose and mixtures thereof. More preferably, the rheology modifier is hydroxyethyl cellulose. The rheology modifier is present in an amount from about 0.05 wt. % to about 5.00 wt. %, preferably from about 0.1 wt. % to about 3.0 wt. %, and more preferably from about 0.3 wt. % to about 2.0 wt. % of the aqueous lubricant composition.

In the production of vaginal fluid, estrogens stimulate the deposit of glycogen in vaginal epithelia, which can then be degraded by vaginal bacteria and/or epithelial cells. The resulting glucose is metabolized to lactic acid, which contributes to the acidic nature of the vaginal fluid (pH of 4 or 4.5). In order to approach the acidic environment of vaginal fluid, an organic or weak acid is used in the aqueous lubricant composition of the instant invention. The organic acid can be selected from lactic acid, acetic acid, citric acid, their acceptable salts and mixtures thereof. Preferably, the organic acid is a mixture of lactic acid, citric acid and sodium citrate. Citric acid and sodium citrate are used in conjunction with lactic acid to regulate and maintain a moderate level of pH for the aqueous lubricant composition to reduce the risk of vaginal infections. The organic acid is present in an amount from about 0.03 wt. % to about 2.00 wt. %, preferably, from about 0.1 wt. % to about 1.5 wt. %, more preferably from about 0.25 wt. % to about 1.00 wt. % of the aqueous lubricant composition.

The inventive composition may further include inorganic and/or organic salts. Notable salts include sodium chloride, potassium chloride and mixtures thereof. The amount of salts used in the composition is preferably from about 0.05 wt. % to about 2.00 wt. %, more preferably from about 0.1 wt. % to about 1.0 wt. % of the aqueous lubricant composition.

At least one preservative may be added to the composition to prevent microbial growth and to lengthen the storage time of the aqueous lubricant composition. Notable preservatives are selected from sorbic acid and its salts, benzoic acid and its salts, and disodium EDTA. A preferred preservative is a hydroxybenzoate. More preferably, the hydroxybenzoate is methyl paraben. The amount of preservative used is from about 0.05 wt. % to about 1.00 wt. %.

The inventive composition may include at least one polyhydric alcohol selected from sorbitol, mannitol, glycols, glycerol and mixtures thereof. Preferably, the polyhydric alcohol is glycerol. However, it must be noted that the amount of polyhydric alcohol in the lubricant should be minimized, such that the amount of polyhydric alcohol is less than 10 wt. %, preferably less than 5 wt. % of the aqueous lubricant composition.

The amount of water present in the aqueous lubricant composition is from about 80 wt. % to 98 wt. %, preferably from about 85 wt. % to 97 wt. %, and more preferably from about 90 wt. % to 95 wt. % of the aqueous lubricant composition.

The aqueous lubricant composition has a viscosity ranging from about 500 cps to about 10,000 cps, preferably from about 2,000 cps to about 8,000 cps. The aqueous lubricant composition has an osmolality from about 150 to about 1,500 mOsm/kg.

The aqueous lubricant composition also provides a relative lubricity of at least 20 during a friction contact test of 420 seconds. The aqueous lubricant composition further provides a normalized lubricity of at least 25% during a friction contact test of 420 seconds. Further, the aqueous lubricant composition has a pH of between 5.5 and 7.0.

Despite the fact that the aqueous lubricant composition contains at least 80 wt. % water, it does not dry out quickly. Unexpectedly, the composition has a long lasting lubricity, which is superior to the marketed water-, silicone-, and emulsion-based lubricants.

Additionally, this composition has a low osmolality compared to water-based lubricants that are currently on the market.

The composition may additionally include fatty acids, albumin, vitamins, particularly vitamin E, mucins, carbohydrate, immunoglobins, and other macromolecules, as well as botanicals such as aloe. The composition may further include functional ingredients that are designed to cause physiological or physical changes in the area to which they are applied. These actives range from ingredients that self-warm when exposed to moisture, e.g. polyols, ingredients that act on nerve endings to simulate a perceived sensation such as warming, cooling and/or tingling, and ingredients that increase localized blood flow, e.g. vasodilators.

Warming Agents

As used herein warming agents refer to compounds that impart heating or warming sensation upon topical application to the skin, oral cavity, throat or mucous membrane. Warming agents may be selected from the group consisting of capsaicin, gingerol, vanillyl ethyl ether, vanillyl propyl ether, vanillyl butyl ether, vanillyl pentyl ether, vanillyl hexyl ether, vanillyl butyl ether acetate, 4-(1-menthoxymethyl)-2-phenyl-1,3-dioxolan, 4-(1-menthoxymethyl)-2-(3',4'-dihydroxyphenyl)-1,3-dioxolan, 4-(1-menthoxymethyl)-2-(2'-hydroxy-3'-methoxyphenyl)-1,3-dioxolan, 4-(1-menthoxymethyl)-2-(4'-methoxyphenyl)-1,3-dioxolan, 4-(1-menthoxymethyl)-2-(3',4'-methylenedioxyphenyl)-1,3-dioxolan, 4-(1-menthoxymethyl)-2-(3'-methoxy-4'-hydroxyphenyl)-1,3-dioxolan, red pepper oil, red pepper oleoresin, ginger oleoresin, nonylic acid vanillyl amide, *Spilanthes acmella* extract, *Zanthoxylum alatum* extract, *Zanthoxylum piperitum* extract, sanshool I, sanshool II, sanshoamide, black pepper extract, chavicine, piperine, spilanthol, or those warming agents disclosed in U.S. Pat. No. 6,780,443, which is hereby incorporated by reference in its entirety.

As would be understood by one of ordinary skill in the art, the same compound may act differently depending on its use level in the composition. For example, a compound may act as a warming agent at a certain use level, yet the same compound will act as a tingling sensate at a higher use level.

Cooling Agents

When cooling agents (also known as cooling sensates) are added to compositions containing warming agents, the cooling agent increases the warming effect of the warming agent. See, e.g. U.S. Pat. No. 6,780,443, which is hereby incorporated by reference. Accordingly, topical warming compositions of the present invention may contain a "cooling agent." In embodiments in which a warming effect is desired, the compositions should contain higher amounts of warming agents than cooling agents.

It has also been found that a topical cooling composition containing a cooling agent (and smaller amounts of or no warming agent) increases the cooling effect of the cooling agent. Therefore, the present invention also provides compositions that include a cooling agent contained in a silicone-containing fluid carrier. These compositions contain a majority of a cooling agent, based on the total amount of sensates added to the composition.

Cooling sensates which may be included in compositions of the present invention include, but are not limited to, menthol, menthone, camphor, pulegol, isopulegol, cineol, mint oil, peppermint oil, spearmint oil, eucalyptus oil, 3-1-menthoxypropane-1,2-diol, N-alkyl-p-menthane-3-carboxamide, 3-1-menthoxy-2-methylpropane-1,2-diol, p-menthane-3,8-diol, 2-1-menthoxyethane-1-ol, 3-1-menthoxypropane-1-ol, 4-1-menthoxybutane-1-ol, 1-(2-hydroxy-4-ethylcyclohexyl)-ethanone, menthyl 3-hydroxybutanoate, menthyl lactate, menthone glycerin ketal, 2-(2-1-menthyloxyethyl)ethanol, menthyl glyoxylate, N-methyl-2,2-isopropylmethyl-3-methylbutanamide, menthyl 2-pyrrolidone-5-carboxylate, monomenthyl succinate, alkali metal salts of monomenthyl succinate, and alkali earth metal salts of monomenthyl succinate, monomenthyl glutarate, alkali metal salts of monomenthyl glutarate, alkali earth metal salts of monomenthyl glutarate, N-[[5-methyl-2-(1-methylethyl)cyclohexyl]carbonyl]glycine, p-menthane-3-carboxylic acid glycerol ester, Menthol propylene glycol carbonate; Menthol ethylene glycol carbonate, and 6-isopropyl-3,9-dimethyl-1,4-dioxaspiro[4.5]decan-2-one.

Other cooling senates are disclosed in U.S. Pat. Nos. 7,030,273 and 6,780,443, which are hereby incorporated by reference in their entirety.

A compound may act as a cooling agent at a certain use level, yet the same compound will act as a tingling sensorial agent at a higher use level. In particular, this is true for menthol and menthol derivatives.

In other embodiments of the present invention, sensates besides warming agents and cooling agents are added in order to enhance the sensate material. For example, in one embodiment of the present invention a tingling sensate is added to enhance the tingling effect of the sensate material.

In general, one or more sensorial agents can be added to the compositions of this invention. Typically, the total amount of sensorial agents will range from 0.01 to less than 1.00 wt. % of the aqueous lubricant composition.

Example 1

A water-based lubricant composition in accordance with the present invention having the formula shown in Table 1 was prepared as follows:

TABLE 1

Water-Based Lubricant Formulation (Lubricant A)

| Phase | Ingredient | % (w/w) |
|---|---|---|
| A | Deionized water | 94.67 |
|   | Methyl paraben | 0.15 |
| B | Sodium hyaluronate | 0.50 |
| C | Hydroxyethyl cellulose | 0.50 |
| D | Lactic acid | 0.26 |
| E | Urea | 1.00 |
| F | Glycerin | 2.00 |
| G | Citric acid | 0.10 |
|   | Sodium citrate | 0.47 |
|   | Sodium chloride | 0.35 |

In a main vessel, Phase A was mixed and heated up to 62° C. When the temperature reached 62° C., Phase B was added into Phase A and mixed until the composition was completely uniform and free of lumps. Then, Phase C was added to the main vessel and mixed for few minutes until the composition was free of lumps. The main vessel was subsequently cooled to 45° C. While the vessel was cooling down to 45° C., Phase D, Phase E and Phase F were added stepwise and mixed between each addition until every single phase was completely dissolved. When the vessel reached 45° C., all Phase G ingredients were added stepwise, mixing between each addition. Finally, the composition was cooled to 20-23° C. room temperature.

Other examples of compositions according to this invention were also produced with the above-described method with the following ingredients:

TABLE 2

Lubricant B

| Phase | Ingredient | % (w/w) |
|---|---|---|
| A | Deionized water | 94.93 |
|   | Methyl paraben | 0.15 |
| B | Sodium hyaluronate | 0.75 |
| C | Hydroxyethyl cellulose | 0.50 |
| D | Lactic acid | 0.26 |
| E | Urea | 1.00 |
| F | Glycerin | 1.00 |
| G | Citric acid | 0.10 |
|   | Sodium citrate | 0.47 |
|   | Sodium chloride | 0.35 |

TABLE 3

Lubricant C

| Phase | Ingredient | % (w/w) |
|---|---|---|
| A | Deionized water | 94.17 |
|   | Methyl paraben | 0.15 |
| B | Sodium hyaluronate | 0.50 |
| C | Hydroxyethyl cellulose | 1.00 |

TABLE 3-continued

Lubricant C

| Phase | Ingredient | % (w/w) |
|---|---|---|
| D | Lactic acid | 0.26 |
| E | Urea | 1.00 |
| F | Glycerin | 2.00 |
| G | Citric acid | 0.10 |
|   | Sodium citrate | 0.47 |
|   | Sodium chloride | 0.35 |

The lubricant formulations described above have a viscosity ranging from 500 cps to 10,000 cps, preferably from about 2,000 to 4,000 cps. The aqueous lubricants can be used as personal lubricants or they can be applied onto a condom in a conventional fashion. The aqueous lubricant composition can be applied to the interior or the exterior of a condom. The coated condom may then be foil-wrapped using procedures common to the art. For coating purposes, 0.45 g to 0.75 g of the lubricant is applied to the exterior surface of the condom, and/or 0.2 to 0.4 g of the aqueous lubricant composition is applied to the interior surface of the condom. The viscosity of the compositions applied to the exterior and the interior surface of a condom can be alike or different.

Example 2

Duration and Decay of Lubricity Compared to Water-Based Lubricants

To demonstrate the long lasting lubricity characteristics of the composition prepared according to Table 1, dynamic lubricity measurements were performed and compared to commercially available products known as K-Y® NATURAL FEELING® and ASTROGLIDE® Liquid Personal Lubricant and Moisturizer, as described in U.S. Pat. No. 6,139,848, which is hereby incorporated by reference in its entirety. K-Y® NATURAL FEELING® and ASTROGLIDE® Liquid Personal Lubricant and Moisturizer are water-based lubricants that contain polyhydric alcohols but no HA. The test method uses a Texture Analyzer to measure the amount of force required to move one surface relative to another. The top surface moved forward and backward (push-pull) while a weight was applied on top of the surface. The bottom surface was fixed. The tested lubricants were applied in a thin layer on the bottom surface to reduce the friction between the two surfaces. The coefficient of friction for each test lubricant was calculated based on the force that was recorded and on the applied weight. The coefficient of friction is inversely proportional to the lubricity of the lubricant also known as "relative lubricity". Relative lubricity was calculated from the coefficient of friction divided data by dividing one (1) numeral to the coefficient of friction value. The test ran for 420 seconds.

Figure 1:
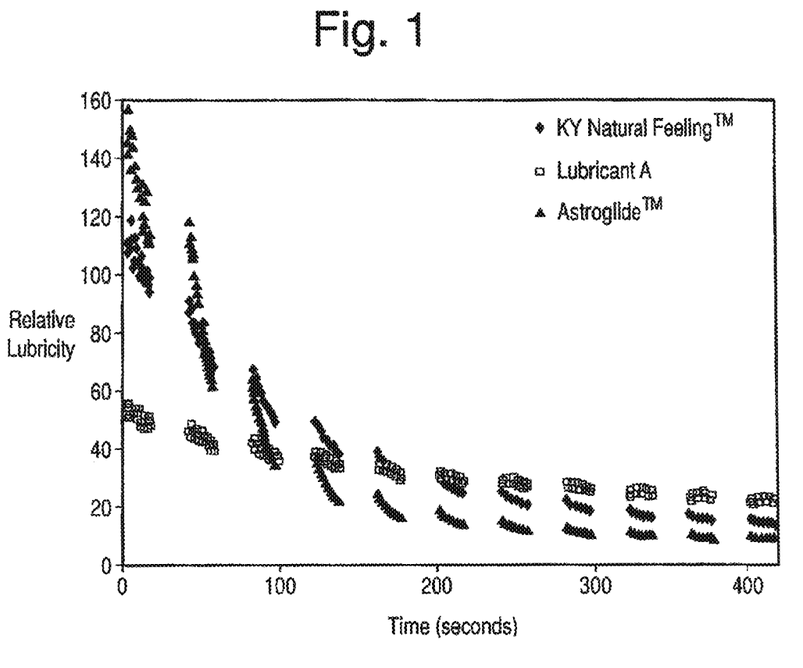
FIG. 1 shows the relative lubricity of the inventive lubricant versus conventional aqueous lubricants.

As illustrated in FIG. 1, although the initial lubricity value of Lubricant A is lower than the comparative lubricants, the relative lubricity of Lubricant A is steady, between 60 and 20 during the 420 second test period, whereas the two competitive water-based lubricants, K-Y® NATURAL FEELING® and ASTROGLIDE® Liquid Personal Lubricant and Moisturizer, experienced a drastic reduction of their relative lubricity from about 160 to below 20 in the span of 420 seconds.

Figure 2:
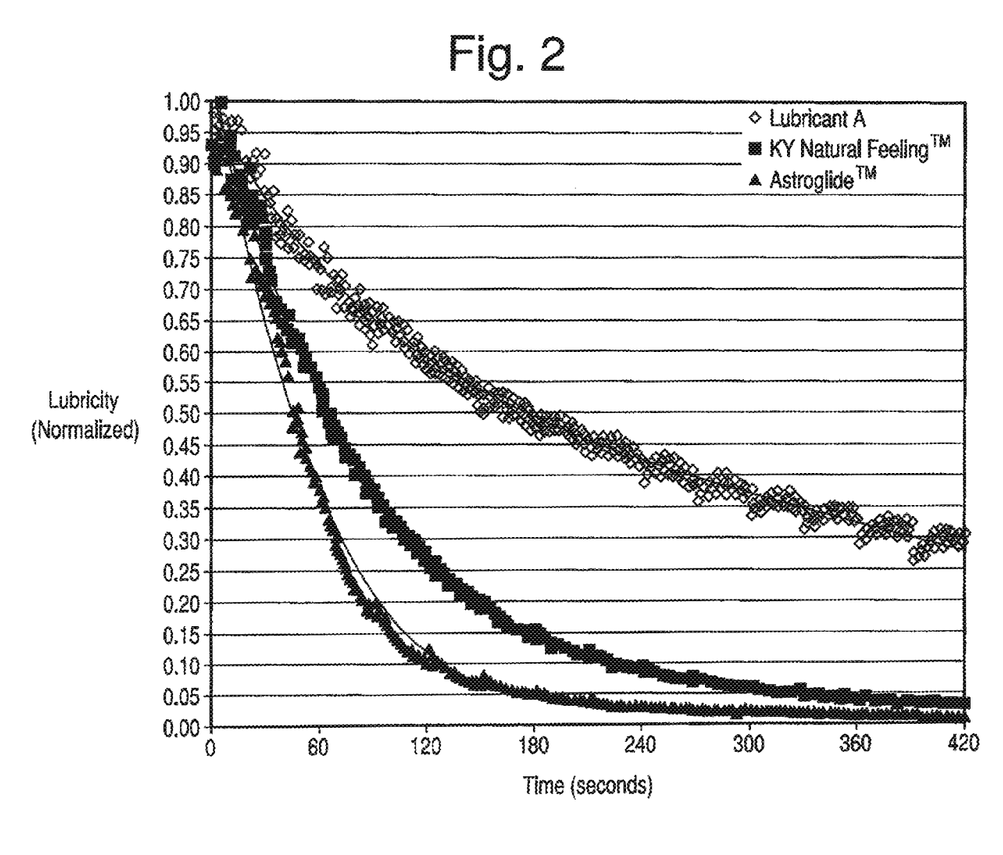
FIG. 2 shows the normalized lubricity of the inventive lubricant versus conventional aqueous lubricants.

While the initial value of lubricity at t=0 is an important parameter in assessing the performance of a lubricant, one should also consider the decay of lubricity. A lubricant with a high initial lubricity value but with a fast decay of lubricity is not expected to provide long lasting lubrication benefits. On the contrary, a lubricant with a low decay of lubricity decay can deliver such benefits. To compare the decay of lubricity of Lubricant A versus the comparative water-based lubricants, the relative lubricity data was normalized. Through normalization, the effect of the initial lubricity value on the final lubricity (at t=420 s) was eliminated. FIG. 2 illustrates the normalized lubricity of Lubricant A versus comparative commercially available lubricant compositions. FIG. 2 shows that Lubricant A still retained about 25% of normalized lubricity, as compared to K-Y® NATURAL FEELING® and ASTROGLIDE® Liquid Personal Lubricant and Moisturizer, which both had less than 5% of normalized lubricity left by the end of the 420 second test period.

In addition to the long lasting lubricity, Lubricant A composition also has low osmolality (656 mOsm/kg, measured value). This is about 7 times lower than K-Y® NATURAL FEELING® osmolality (4523 mOsm/kg) and about 12 times lower than ASTROGLIDE® osmolality (8064 mOsm/kg). The osmolality of the two marketed personal lubricants was disclosed in *AIDS Research and Human retroviruses*, 27, 1-6, 2011.

Example 3

Duration and Decay of Lubricity Compared to Silicone-Based Lubricants

Figure 3:
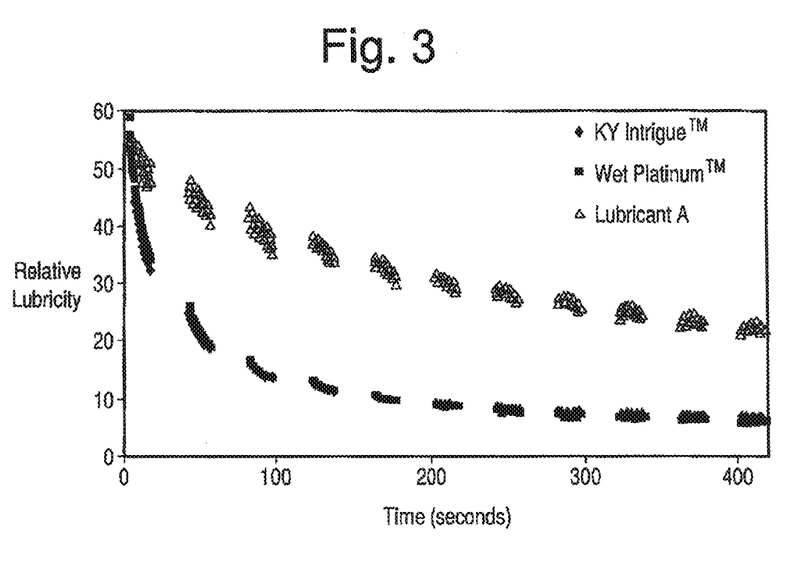
FIG. 3 shows the relative lubricity of the inventive lubricant versus conventional silicone-based lubricants.
Figure 4:
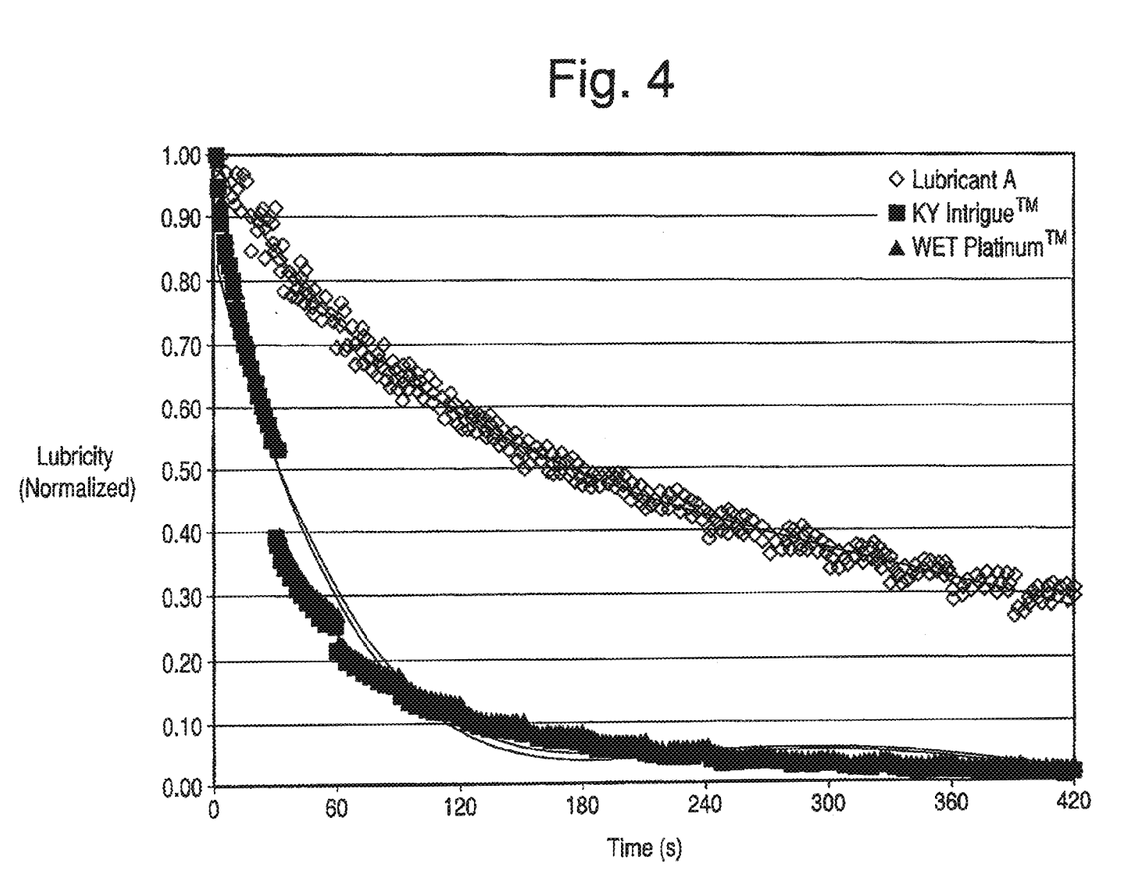
FIG. 4 shows the normalized lubricity of the inventive lubricant versus conventional silicone-based lubricants.

For those skilled in the art, it is well known that silicone-based lubricants provide superior long lasting benefits to water-based lubricants. Although Lubricant A is a water-based composition, surprisingly its lubricity lasted longer than that of two commercially available silicone-based lubricants, K-Y® INTRIGUE® and WET PLATINUM® during the dynamic lubricity measurement test, as illustrated in FIG. 3. The initial lubricity value of Lubricant A is comparable to that of K-Y® INTRIGUE® and WET PLATINUM®. However, in the first 100 seconds of the 420 second test period the relative lubricity of Lubricant A decreased from 58 to about 40, whereas the relative lubricity of the competitive lubricants decreased from 60 to 13. The lesser decay of relative lubricity of Lubricant A decreased from 58 to about 40, whereas the relative lubricity of the competitive lubricants decreased from 60 to 13. The lesser decay of lubricity of Lubricant A is even better displayed by normalizing the relative lubricity data as indicated in FIG. 4. Lubricant A retains about 25% of lubricity as compared to K-Y® INTRIGUE® and WET PLATINUM®, which both had less than 5% of lubricity left by the end of the 420 second test period.

Figure 5:
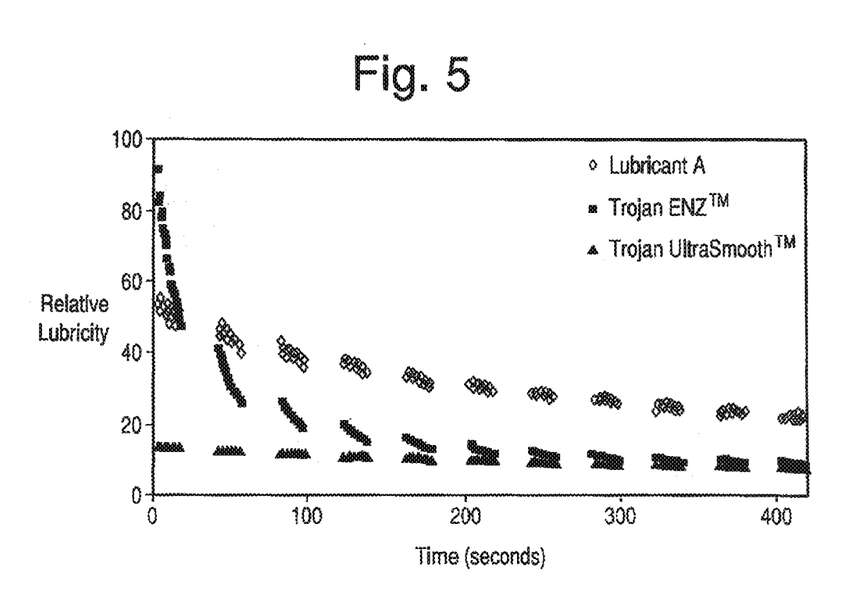
FIG. 5 shows the relative lubricity of the inventive lubricant versus conventional silicone-based lubricants.
Figure 6:
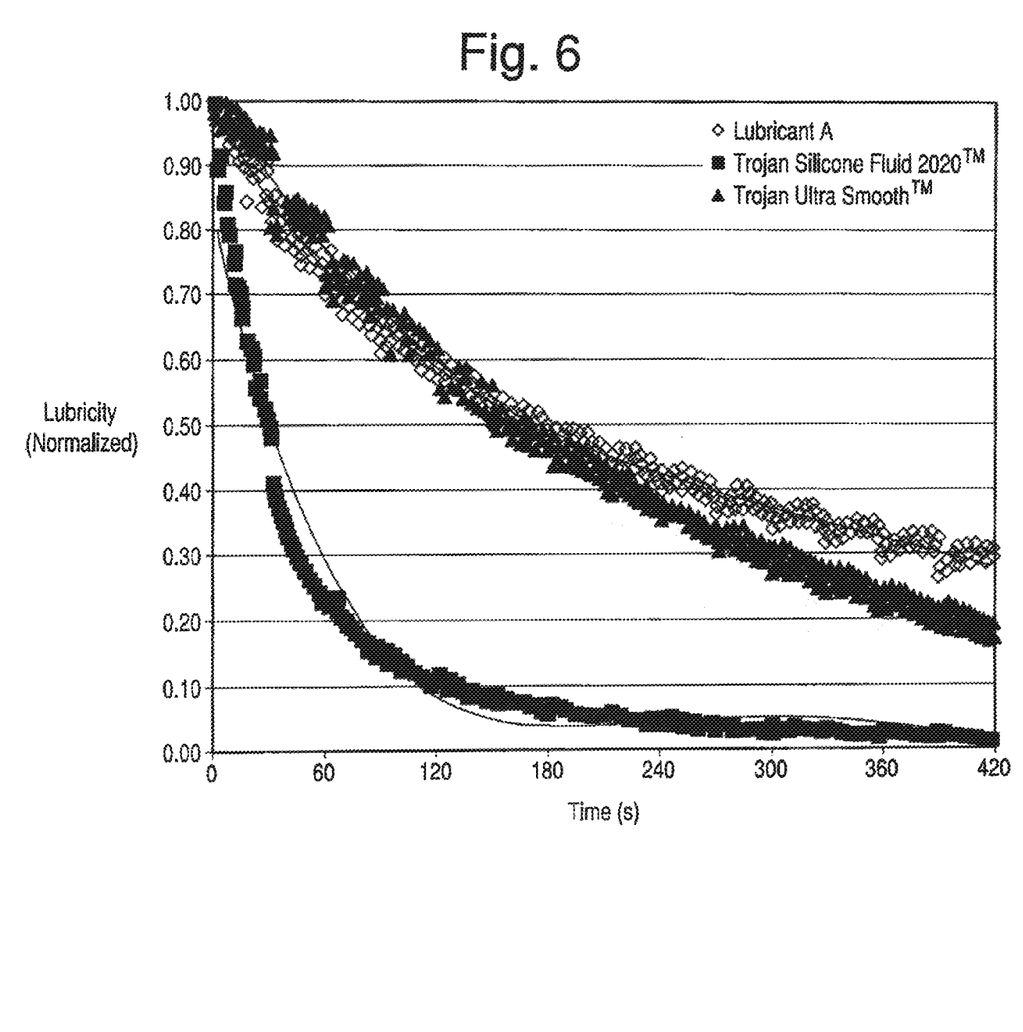
FIG. 6 shows the normalized lubricity of the inventive lubricant versus conventional silicone-based lubricants.

Furthermore, the compositions of Lubricant A can be used not only as a standalone lubricant, but also as a lubricant on a condom. FIG. 5 shows the relative lubricity of Lubricant A compared to TROJAN® ENZ® (TROJAN® Silicone Fluid 200) and TROJAN® UltraSmooth condom lubricants, which are silicone-based lubricants. When comparing the decay of lubricity, FIG. 6 shows that Lubricant A has much less decay than TROJAN® ENZ® and comparable to TROJAN® UltraSmooth decay.

Example 4

Duration and Decay of Lubricity Compared to Emulsion-Based Lubricants

Figure 7:
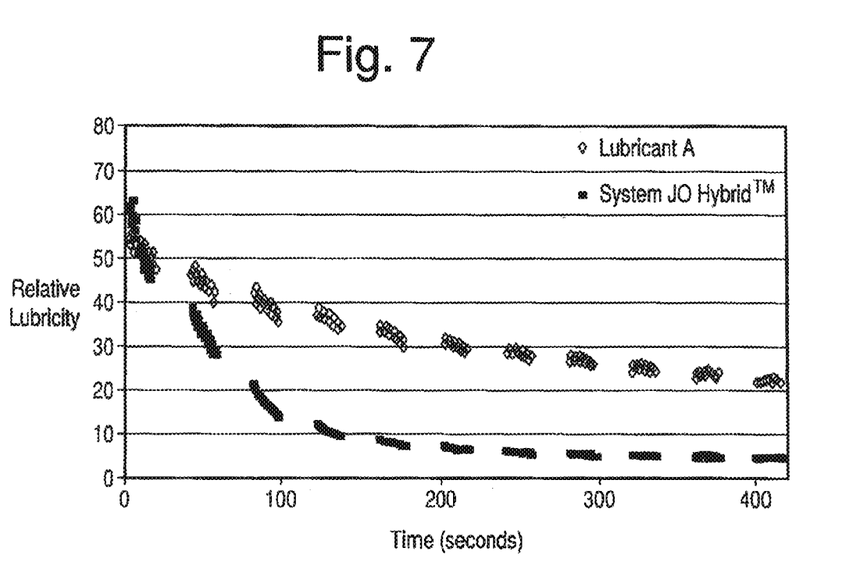
FIG. 7 shows the relative lubricity of the inventive lubricant versus conventional emulsion-based lubricants.
Figure 8:
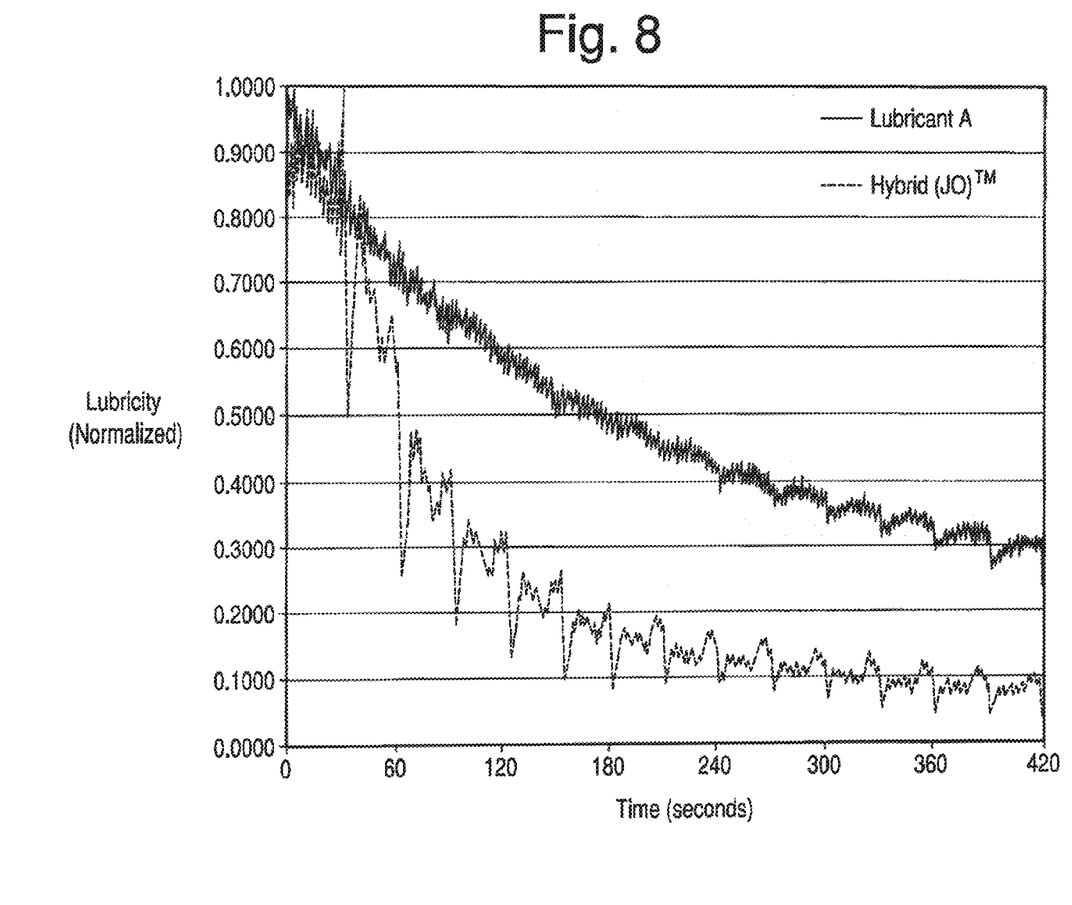
FIG. 8 shows the normalized lubricity of the inventive lubricant versus conventional emulsions-based lubricants.

Emulsion-based lubricants deliver the benefits of both water-based and silicone-based lubricants. An example of such lubricant is the commercially available SYSTEM JO® Hybrid. Direct comparison of Lubricant A composition to SYSTEM JO® Hybrid reveals that Lubricant A has a longer lasting and lesser decay of lubricity than SYSTEM JO® Hybrid (see FIG. 7 and FIG. 8).

Although urea and lactic acid were included in these Examples, it is also possible to prepare the inventive composition without lactic acid and urea. Those skilled in the art will appreciate that without those ingredients, a pH adjuster, such as sodium hydroxide, may well be necessary to achieve the desired pH level, generally about 5.5 to 7.0.

The invention claimed is:

1. An aqueous lubricant composition consisting essentially of:
    i) a salt selected from the group consisting of sodium chloride, potassium chloride, and mixtures thereof;
    ii) an organic acid selected from the group consisting of acetic acid, citric acid, their salts and mixtures thereof;
    iii) hyaluronic acid having a molecular weight of between 1.3 MDa and 1.8 MDa;
    iv) a cellulose-based rheology modifier; and
    v) water, wherein said water is present in an amount of at least 90 wt. % of said composition.

2. The aqueous lubricant composition of claim 1, wherein said hyaluronic acid is present in an amount of about 0.4 to about 1.0 wt. % of said composition.

3. The aqueous lubricant composition of claim 1, wherein said cellulose-based rheology modifier is selected from the group consisting of hydroxylpropyl cellulose, carboxylmethyl cellulose, hydroxyethyl cellulose and mixtures thereof.

4. The aqueous lubricant composition of claim 3, wherein said rheology modifier is hydroxyethyl cellulose.

5. The aqueous lubricant composition of claim 1, having a viscosity of about 2,000 cps to about 8,000 cps.

6. The aqueous lubricant composition of claim 1, having an osmolality of about 150 mOsm/kg to 1,500 mOsm/kg.

7. The aqueous lubricant composition of claim 1, having a pH of about 5.5 to 7.0.

8. The aqueous lubricant composition of claim 1, containing less than 5 wt. % of at least one polyhydric alcohol.

9. The aqueous lubricant composition of claim 1, further including a preservative.

10. The aqueous lubricant composition of claim 1, wherein said organic acid is present in an amount of from about 0.05 wt. % to about 1.00 wt. % of said composition.

11. The aqueous lubricant composition of claim 3, wherein said rheology modifier is present in an amount of from about 0.05 to about 5.00 wt. % of said composition.

12. The aqueous lubricant composition of claim 1, wherein said at least one salt is present in an amount of from about 0.1 to about 1.0 wt. % of said composition.

13. The aqueous lubricant composition of claim 8, further including a preservative.

14. A condom containing a coating on the inside thereof, the outside thereof or both of the aqueous lubricant composition of claim 1.

15. The aqueous lubricant composition of claim 1, wherein said composition further includes an additive selected from the group consisting of at least one vitamin, mucin, botanical, fatty acids and mixtures thereof.

16. The aqueous lubricant composition of claim 15, wherein said vitamin is consisting of vitamin E and said botanical is consisting of aloe.

\* \* \* \* \*